United States Patent [19]

Pohlman et al.

[11] Patent Number: 4,857,964

[45] Date of Patent: Aug. 15, 1989

[54] APPARATUS FOR PRINTING CUSTOMIZED PHOTOGRAPHIC PRINTS

[75] Inventors: James M. Pohlman, Berkley, Mass.; Joseph A. Manico, Rochester, N.Y.

[73] Assignee: Eastman Kodak Company, Rochester, N.Y.

[21] Appl. No.: 189,435

[22] Filed: May 2, 1988

Related U.S. Application Data

[63] Continuation of Ser. No. 85,670, Aug. 14, 1987, abandoned.

[51] Int. Cl.⁴ .............................................. G03B 27/52
[52] U.S. Cl. ........................................ 355/40; 355/74; 355/75; 355/39; 355/114
[58] Field of Search ................ 355/40, 46, 75, 74, 355/114, 39, 41, 42, 72

[56] References Cited

U.S. PATENT DOCUMENTS

| | | | |
|---|---|---|---|
| 1,303,418 | 5/1919 | Tornsjo | 355/40 |
| 2,188,843 | 1/1940 | Pappajion | 355/40 |
| 2,460,060 | 1/1949 | Butler | 355/40 |
| 2,580,270 | 12/1951 | Badgley et al. | 355/41 |
| 2,829,556 | 4/1958 | Carter | 355/46 |
| 3,292,485 | 12/1966 | Mey | 355/74 |

Primary Examiner—Monroe H. Hayes

[57] ABSTRACT

A photographic printer is provided for producing customized photographic prints including a customer-supplied image and an operator-selected artwork. The printer includes a new and improved film gate for supporting at least one printable artwork substantially coplanar with and adjacent to the customer-supplied artwork. The film gate further includes means for supporting a neutral density filter in registry with the artwork. In operation, the printer lamphouse and printing lens are used to print the artwork, during the same exposure as the negative, in a selected position relative to the negative. The printer can be used, for example, to produce customized greeting cards including a customer-supplied image and a holiday greeting.

11 Claims, 4 Drawing Sheets

APPARATUS FOR PRINTING CUSTOMIZED PHOTOGRAPHIC PRINTS

This is a continuation of application Ser. No. 085670, filed Aug. 14, 1987, now abandoned.

The present invention relates generally to photographic printing and more specifically to the making of customized photographic prints such as greeting cards.

BACKGROUND OF THE INVENTION

There exists a well recognized market for manufacturing customized greeting cards including personalized picture images provided by customers. Such greeting cards provide, for example, the opportunity for a customer to include a picture of his family on a holiday greeting card.

One method of producing such customized greeting cards comprises providing a pre-printed card including a cut-out or aperture into which a customer-supplied print can be mounted. A customer then purchases such a card, and inserts his own print into the cut-out. The resulting customized greeting card, however, does not provide a professional appearance. Further, such a greeting card is expensive, requiring a customer to purchase the pre-printed card and to supply a finished photographic print.

Another method of providing such customized greeting cards is shown in U.S. Pat. No. 3,136,232 to Shoberg et al. The Schoberg et al. reference shows an easel including a contact printer situated on the edge thereof. The easel is used in combination with a photographic printer/enlarger, and functions to support a portion of photographic paper onto which a print is projected. The contact printer is used to print customized artwork. such as a holiday greeting, onto the edge of the photographic paper portion. The result is a customized photographic print including a customer supplied picture image and a selected, customizing artwork.

Schoberg et al. suffers from the disadvantage of requiring the additional contact printer to print the customizing artwork. Such a contact printer is expensive and complex, requiring at a minimum a light source, power, a control mechanism for the light source, and accompanying hardware. The easel taught by Schoberg et al. thus adds significantly to the cost and maintenance of a basic photographic printer.

OBJECTS OF THE INVENTION

The principle object of the present invention is to provide a simple and economical method and apparatus for providing a customized photographic print including a customer-supplied picture image and customizing artwork.

Another object of the present invention is to provide a method and apparatus for providing economical, customized photographic prints having a professional appearance.

Yet another object of the present invention is to provide a method and apparatus for providing customized photographic prints which requires a minimum of equipment in addition to that supplied standardly with a photographic printer or enlarger.

A further object of the present invention is to provide a customized film gate which can be used with a great number of photographic printers and enlargers, thereby enabling those printers and enlargers to produce customized photographic prints with a minimum of modifications and cost.

SUMMARY OF THE INVENTION

New and improved method and apparatus are provided for producing customized photographic prints, each customized print including a customer-supplied picture image and a selectable, customizing artwork such as a holiday greeting. The method uses a photographic printer including means for projecting light through a film image to expose said film image onto a photographic paper. In accordance with the present method, a printable, selectable artwork is supported in the path of the projected light so as to expose the artwork onto the photographic paper in a selected position relative to the exposure of the film image.

In a preferred embodiment of the invention means are provided for supporting a plurality of printable artworks and for permitting an operator to position a selected one of the artworks substantially coplanar with and adjacent to the customer-supplied film image. Further provided are means for supporting a plurality of neutral density filters and for permitting an operator to position a selected one of the neutral density filters in registry with the selected artwork.

BRIEF DESCRIPTION OF THE DRAWINGS

While the specification concludes with claims defining the features of the invention that are regarded as novel, it is believed that the invention, together with further objects thereof, will be better understood from a consideration of the following description in conjunction with the drawing figures, in which like reference numerals are carried forward, and in which:

DETAILED DESCRIPTION OF THE INVENTION

Figure 1:
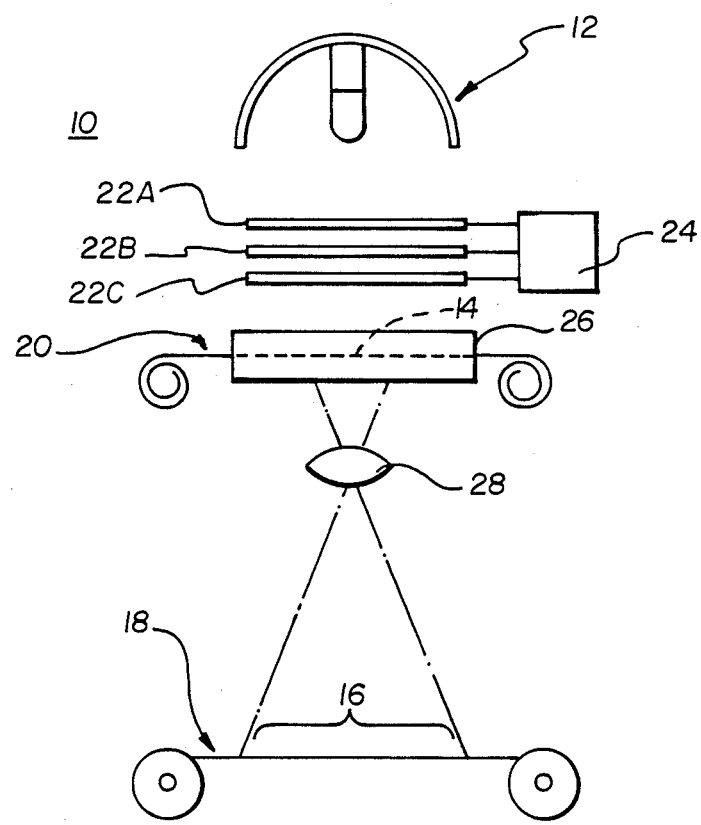
FIG. 1 shows a schematic view of a photographic printer constructed in accordance with the present invention.

Referring now to the drawings, FIG. 1 shows a printer 10 including a light source 12 for projecting light through a selected film image or negative 14 to form an exposure 16 on a portion of a roll of photographic paper 18. Negative 14 comprises a selected one of a disc or roll 20 of customer-supplied negatives.

In accordance with standard features known to those skilled in the art, printer 10 further includes additive or subtractive color filters 22A, 22B, 22C, connected to a controller 24, for controlling the exposure times of the various colors in negative 14. A new and improved film gate 26, described in detail below, is provided for supporting negative 14 and a selectable, printable artwork (not visible in FIG. 1) in the path of the light projected by light source 12. A printing lens 28 is disposed intermediate film gate 26 and photographic paper 18 for imaging film negative 14 and the artwork into a plane of focus on the photographic paper.

Figure 2:
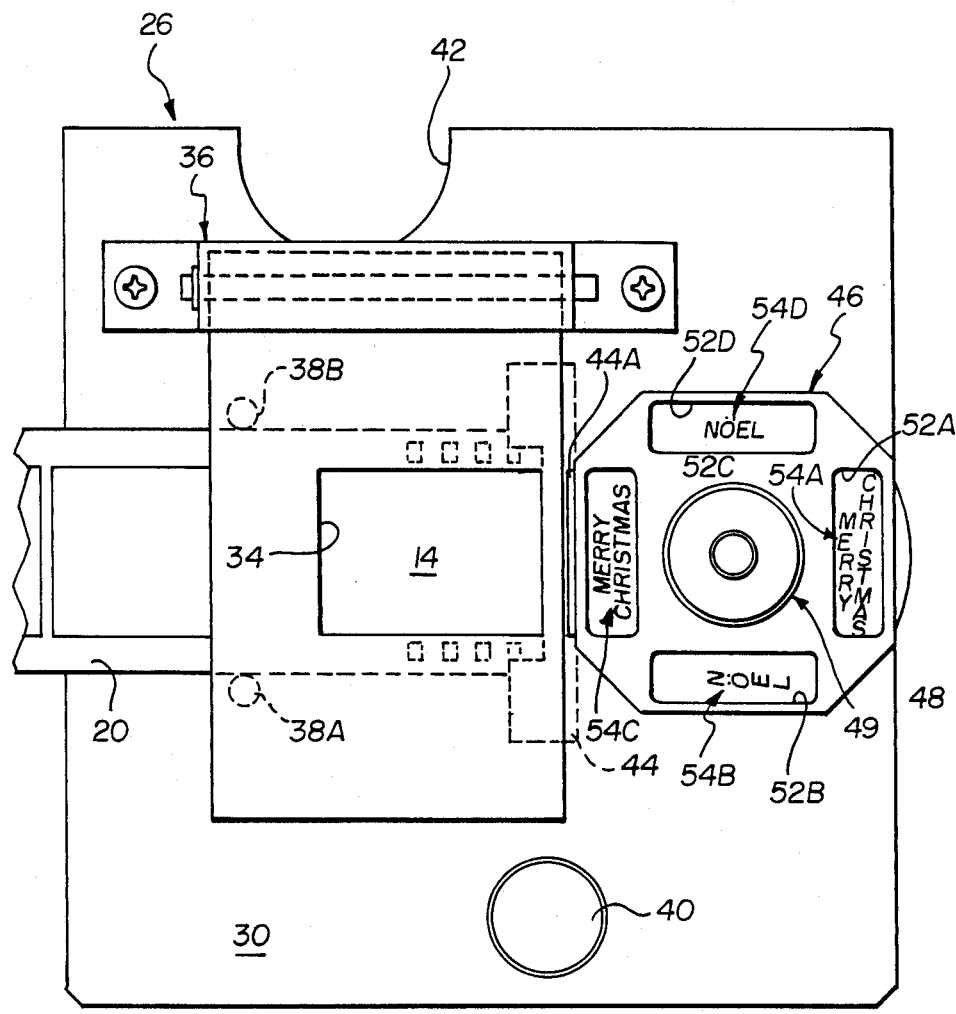
FIGS. 2, 3, and 4, show top, side section and bottom views, respectively, of the custom film gate of FIG. 1.
Figure 3:
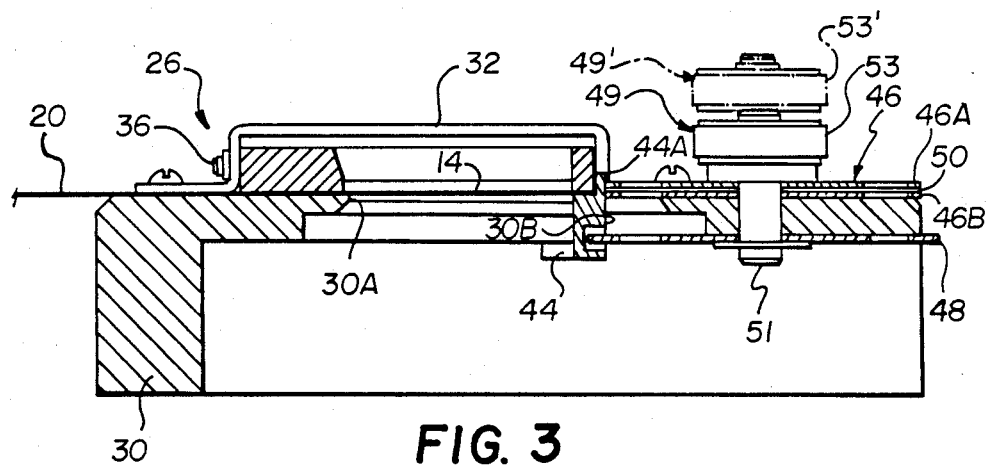
Figure 4:
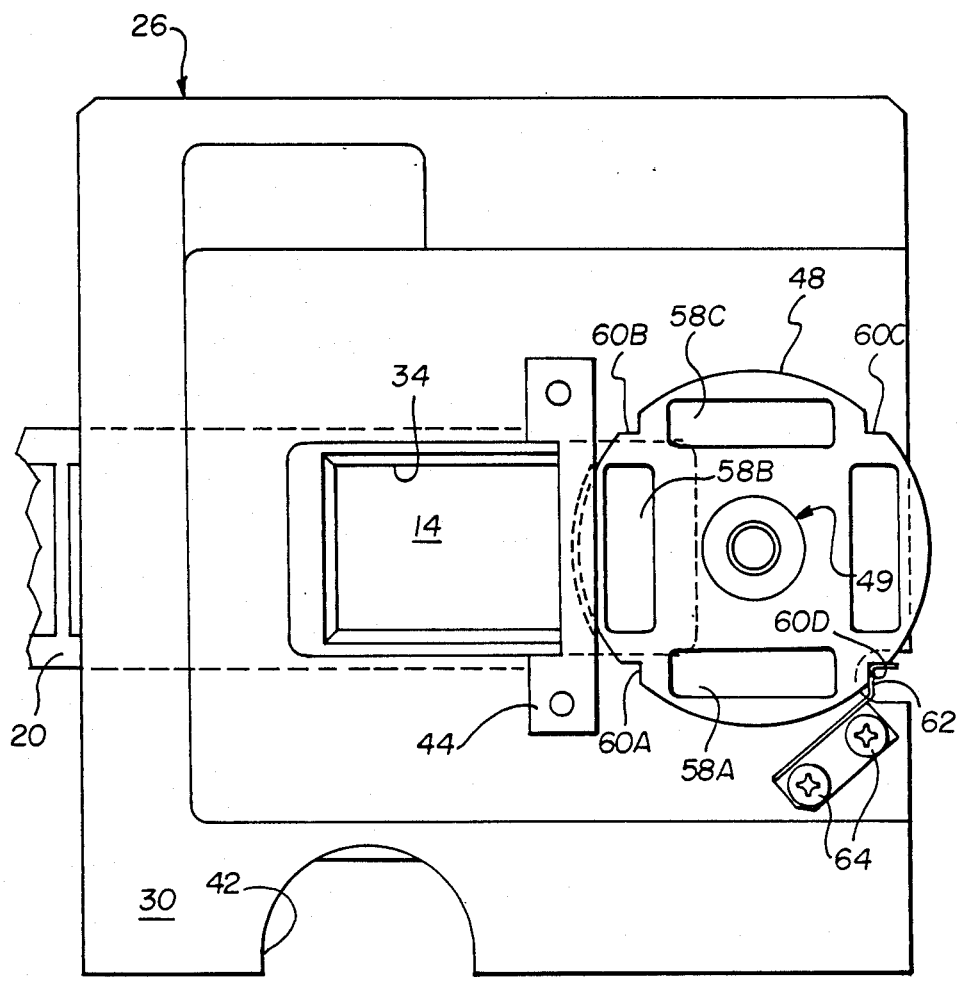

Referring now to FIGS. 2, 3, and 4, film gate 26 comprises an opaque base 30 defining first and second rectangular apertures 30A, 30B (FIG. 3). In the embodiment shown and described herein, aperture 30A is approximately the size of an exposed 35 mm negative. Aperture 30B is approximately one fourth the size of aperture 30A, the two apertures being disposed generally adjacent one-another. It will be understood that the size of apertures 30A, 30B is determined by the size of negative 14 and the customized artwork, respectively, the artwork being shown and described in detail below.

Supported on an upper side of base 30 is a frame 32 defining a printing aperture 34. Frame 32 is mounted to base 30 via a hinge 36 such that, with frame 32 in the closed position (as shown in FIGS. 2-4), printing aperture 34 is substantially in registry with base aperture 30A. An opposing pair of guide pins 38A, 38B are mounted on base 30 underneath frame 32 and spaced the width of filmstrip 20. As described in detail below, guide pins 38A, 38B are used to position negative 14 in alignment with apertures 30A, 34. A mounting aperture 40 and notch 42 are provided for securing film gate 26 in position with mating features (not shown) on printer 10. A bracket 44 is mounted on the underside of base 30 and includes a bar-shaped stop 44A projecting through the base and adjoining a side of frame 32.

Further provided with film gate 26 are generally opposing, rotatable message and filter wheels, 46, 48, respectively. A knob assembly 49 includes a shaft 51 extending through message wheel 46 and filter wheel 48 and being secured to base 30, with the message and filter wheels being rotatable about the axis of the shaft. A thumbwheel 53 is secured to shaft 51 by a threaded screw connection (not visible). As shown in solid line in FIG. 3, with thumbwheel 53 screwed tightly onto shaft 51, message and filter wheels 46, 48, respectively, are positioned adjoining opposite sides of base 30, with a selected side of the message wheel abutting stop 44A.

As is best shown in FIG. 3, message wheel 46 overlies the top of base 30 adjacent stop bar 44A, and comprises a pair of opposing, octagonally-shaped plates, 46A, 46B, sandwiching an intermediate, changeable, artwork medium 50. Plates 46A, 46B each define four apertures, the apertures being in registry to provide four apertures 52A, 52B, 52C, 52D extending through message wheel 46 and positioned adjacent respective octagonal sides thereof. Artwork medium 50 comprises, for example, a film base including four separate messages 54A, 54B, 54C, 54D, each message being centered in a corresponding aperture 52A-52D. Plates 46A, 46B comprise an opaque, relatively stiff material for supporting artwork medium 50, for example a metal such as aluminum. Message wheel 46 is sized such that, in the operating position shown in solid line in FIGS. 2-4, a selected edge adjacent a selected message 54A-54D can be positioned snugly adjoining stop bar 44A. The selected message 54A-54D is concomitantly positioned in registry with aperture 30B.

Filter wheel 48, as is best shown in FIG. 4, comprises a circular portion of film base having four neutral density filter regions 58A, 58B, 58C, 58D disposed thereon. As will be discussed in further detail below, each of filter regions 58A-58D comprises a different neutral density characteristic. Filter wheel 48 includes four notches 60A, 60B, 60C, 60D spaced about the periphery thereof. A detent 62 is secured to base 30 with screws 64 for engaging a selected notch 60A-60D. Filter wheel 48 is sized, and neutral density filter regions 58A-58D are spaced, such that a selected neutral density filter region can be positioned in registry with aperture 30B and hence in registry with a selected message 54A-54D.

In operation, filmstrip 20 is trimmed such that negative 14 is on an end thereof. Frame 32 is pivoted away from base 30, and film strip 20 is positioned between pins 38A, 38B and abutting stop 44A. Frame 32 is then pivoted down to hold negative 14 in place. Negative 14 is thus in registry with apertures 30A and 34 as shown in FIGS. 2-4.

An operator then selects a desired message 54A-54D to be printed with negative 14, and rotates message wheel 46 until that message is positioned adjoining stop 44A. As illustrated in dot-dashed-line, and indicated by primed reference numerals in FIG. 3, message wheel 46 is rotated by unscrewing thumbwheel 53 to the 53' position on shaft 51, lifting the message wheel clear of stop 44A, and rotating the message wheel until the selected message 54A-54D is positioned adjacent the stop. Message wheel 46 is then lowered back onto base 30, and the thumbwheel 53' is tightened back down from its dot-dashed position 53' to its solid line position 53 on shaft 51 to hold the message wheel securely in position (as shown in solid line in FIGS. 2-4). The selected message, for example message 54C as shown in FIG. 2, is thus situated in registry with aperture 30B in base 30.

In addition to selecting a message 54A-54D, the operator further selects a neutral density filter region 58A-58D to position in registry with the selected message. The selected neutral density filter is positioned by rotating filter wheel 48, with detent 62 engaging the appropriate notch 60A-60D to hold the selected neutral density filter securely in position. It will be appreciated that the function of neutral density filter regions 58A-58D are to provide proper exposure of the selected artwork 54A-54D. The selection of a proper neutral density filter will, of course, be a function of the characteristics of both negative 14 and the selected artwork 54A-54D, and is well within the purview of those skilled in the art.

Figure 5:
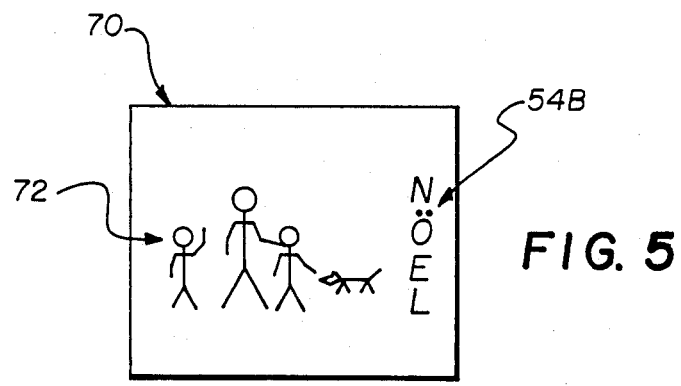
FIGS. 5 and 6 show drawings representative of custom prints produced in accordance with the present invention.
Figure 6:
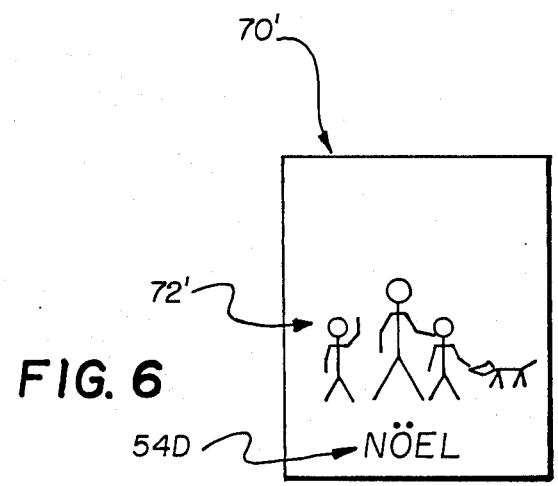

After positioning negative 14, a selected artwork 54A-54D, and a selected neutral density filter region 58A-58D as described above, an exposure is made in printer 10 (FIG. 1) in accordance with standard printing procedures. Referring now to FIGS. 5 and 6, the final, customized print 70, 70', will comprise the print of the customer supplied negative 14, indicated generally at 72, 72', adjoined by the operator-selected artwork (message 54B in FIG. 5 and message 54D in FIG. 6).

While message wheel 46 has been described herein as comprising relatively simple, stencil-type messages 54A-54D, it will be understood that the invention is not so limited. Messages 54A-54D could comprise, for example, more complex artworks such as cartoon-type figures or even photographic scenes. It will be appreciated that the number of artworks 54 and neutral density filters 58 are not limited to the four shown. Further, it will be understood that it will be necessary to select lens 28 to have a focal length appropriate to image both negative 14 and the selected artwork 54 onto photographic paper 18. Such lenses are readily commercially available, and the selection of such a lens is well within the purview of those skilled in the art.

There is thus provided a color photographic printer, including a customized print gate, for producing customized prints including selectable artworks in combination with a customer-supplied image. The invention may be implemented in substantially any printer by incorporating the customized film gate. Further, the invention provides the substantial advantage of utilizing all of the major components already present in a printer, including the light source, exposure control apparatus, printing lens, and paper transport and handling mechanism.

While a preferred embodiment of the invention has been illustrated and described, it will be clear that the invention is not so limited. Numerous modifications, changes, variations, substitutions and equivalents will occur to those skilled in the art without departing from the spirit and scope of the present invention.

What is claimed is:

1. A photographic printer for exposing a film image and a print image onto a photosensitive medium, the printer comprising:
    a. base means for supporting the film image, the base means including a first side, an opposing second side, a first opening extending between the first and second sides over which the film image is supported, and a second opening extending between the first and second sides;
    b. means for supporting the print image;
    c. a single light source for projecting light (i) through the first opening to expose the film image onto the photosensitive medium and (ii) through the second opening;
    d. first means for filtering the light prior to reaching the photosensitive medium;
    e. means for connecting the print image supporting means to the base means in a manner that the print image supporting means is movable to a first location in general alignment with the second opening to allow the light to expose the print image onto the photosensitive medium; and
    f. means for connecting the filtering means to the base means in a manner that the filtering means is movable to a second location in general alignment with the second opening in order to filter the light travelling through the second opening which exposes the print image onto the photosensitive medium.

2. The printer as set forth in claim 1 additionally comprising second means for filtering the light which exposes the film image onto the photosensitive medium.

3. The printer as set forth in claim 1 additionally comprising:
    a. shaft means, having an axis, which extend through the base means;
    b. means for connecting the print image supporting means to the shaft means in a manner that the print image supporting means is rotatable about the shaft axis to the first location; and
    c. means for connecting the filtering means to the shaft means in a manner that the filtering means is rotatable about the shaft axis to the second location.

4. The photographic printer as set forth in claim 3 wherein the print image supporting means is located at the first side of the base means and the filtering means is located at the second side of the base means.

5. The photographic printer as set forth in claim 4 wherein the print image supporting means is located coplanar with a plane of the film image.

6. A photographic printer for exposing a film image and a print image onto a photosensitive medium, the printer comprising:
    a. base means having first and second openings therethrough, the base means including a first alignment member;
    b. means, attached to the base means, for supporting the film image in general alignment with the first opening;
    c. means, having a second alignment member, for supporting the print image;
    d. means for projecting light (i) through the first opening to expose the film image onto the photosensitive medium and (ii) through the second opening; and
    e. means for connecting the print image supporting means to the base means in a manner that the print image supporting means is movable from (i) a first position where the second alignment member of the print image supporting means engages the first alignment member of the base means to secure the print image in general alignment with the second opening in order to expose the print image onto the photosensitive medium, and (ii) a second position where the second alignment member does not engage the first alignment member and the print image is not in general alignment with the second opening.

7. The printer as set forth in claim 6 wherein the connecting means includes (i) shaft means, having a shaft axis, for connecting the print image supporting means to the base means, (ii) means for allowing movement of the print image supporting means away from the base means so that the print image supporting member can be moved about the shaft axis to align the first and second alignment means, as well as (iii) means for allowing movement of the print image support means toward the base means when the first alignment member and the second alignment member are in alignment so that the first alignment member and the second alignment member can be engaged in order to secure the print image in general alignment with the second opening.

8. The printer as set forth in claim 7 wherein:
    a. the first alignment member extends upwardly from the base means to engage the second alignment member in the first position; and
    b. the connecting means includes means for moving the print image supporting means away from the base means on the shaft means so that the second alignment member is clear of the first alignment member to permit movement of the print image support means about the shaft axis.

9. A method for exposing a film image and a print image onto a photosensitive medium, the method comprising the steps of:
    a. supporting the film image by base means which have a first opening over which the film image is supported, and a second opening;
    b. providing a support for the print image;
    c. projecting light from a single source (i) through the first opening to expose the film image onto the photosensitive medium and (ii) through the second opening;
    d. providing a filter for the light prior to reaching the photosensitive medium;
    e. connecting the print image support to the base means in a manner that the print image support is movable to a first location in general alignment with the second opening to allow the light to expose the print image onto the photosensitive medium; and
    f. connecting the filter to the base means in a manner that the filter is movable to a second location in general alignment with the second opening in order to filter the light travelling through the second opening when exposing the print image onto the photosensitive medium.

10. The method as set forth in claim 9 additionally comprising the steps of:
   a. connecting the print image support to the base means by shaft means, having a shaft axis, in a manner that the print image support is rotatable about the shaft axis to the first location; and
   c. connecting the filter to the shaft means in a manner that the filter is rotatable about the shaft axis to the second location.

11. A photographic printer for exposing a film image and a print image onto a photosensitive medium, the printer comprising:
   a. base means for supporting the film image, the base means including a first side, an opposing second side, a first opening extending between the first and second sides, and a second opening extending between the first and second sides;
   b. means for supporting the film image in general alignment with the first opening;
   c. means for supporting the print image in general alignment with the second opening and generally coplanar with a plane of the film image;
   d. a single light source for projecting light (i) through the first opening to expose the film image onto the photosensitive medium and (ii) through the second opening to expose simultaneously the print image onto the photosensitive medium; and
   e. means for selectively controlling the light projected from the light source through the second opening and print image independently of the light projected from the light source through the first opening and film image prior to reaching the photosensitive medium.

* * * * *